US012123837B2

(12) United States Patent
Bloder (10) Patent No.: US 12,123,837 B2
(45) Date of Patent: Oct. 22, 2024

(54) METHOD AND APPARATUS FOR DETERMINING THE CONTENT OF A FOREIGN GAS IN A PROCESS LIQUID

(71) Applicant: Anton Paar GmbH, Graz-Strassgang (AT)

(72) Inventor: Josef Bloder, Gleisdorf (AT)

(73) Assignee: Anton Paar GmbH, Graz-Strassgang (AT)

(*) Notice: Subject to any disclaimer, the term of this patent is extended or adjusted under 35 U.S.C. 154(b) by 409 days.

(21) Appl. No.: 17/313,160

(22) Filed: May 6, 2021

(65) Prior Publication Data

US 2021/0349036 A1 Nov. 11, 2021

(30) Foreign Application Priority Data

May 6, 2020 (AT) .............................. A 50384/2020

(51) Int. Cl.
*G01N 21/84* (2006.01)
*G01K 5/30* (2006.01)
*G01N 7/10* (2006.01)
*G01N 21/3577* (2014.01)
*G01N 21/552* (2014.01)

(52) U.S. Cl.
CPC .............. *G01N 21/84* (2013.01); *G01K 5/30* (2013.01); *G01N 7/10* (2013.01); *G01N 21/3577* (2013.01); *G01N 21/552* (2013.01); *G01N 2021/8405* (2013.01)

(58) Field of Classification Search
CPC ...... G01N 21/84; G01N 7/10; G01N 21/3577; G01N 21/552; G01N 2021/8405; G01N 7/14; G01N 33/14; G01N 21/59; G01K 5/30

USPC ........................................................ 73/31.04
See application file for complete search history.

(56) References Cited

U.S. PATENT DOCUMENTS

| 4,179,918 | A | * | 12/1979 | van Strien | ........... G01N 33/146 73/19.06 |
| 6,138,497 | A | * | 10/2000 | Nix | .......................... G01N 7/14 73/19.1 |
| 6,874,351 | B2 | | 4/2005 | Bloder et al. | |
| 7,588,210 | B2 | | 9/2009 | Haefner | |
| 2003/0029228 | A1 | * | 2/2003 | Bloder | ..................... G01N 7/14 73/53.01 |

(Continued)

FOREIGN PATENT DOCUMENTS

| AT | 409673 B | 10/2002 |
| AT | 512291 B1 | 7/2013 |

(Continued)

*Primary Examiner* — Marrit Eyassu
(74) *Attorney, Agent, or Firm* — Laurence A. Greenberg; Werner H. Stemer; Ralph E. Locher (57) ABSTRACT

A method and an apparatus determine a content of a foreign gas in a process liquid in which a measurement gas, especially $CO_2$, has been dissolved. A concentration of the measurement gas is ascertained and a concentration of the gas mixture formed by the measurement gas and the foreign gas is ascertained, especially via a manometric measurement method. The measurement values are supplied to an evaluation unit. A concentration of the foreign gas is determined on the basis of the ascertained concentration of the measurement gas and the ascertained concentration of the gas mixture.

18 Claims, 3 Drawing Sheets

(56) References Cited

U.S. PATENT DOCUMENTS

| | | | |
|---|---|---|---|
| 2008/0118418 A1* | 5/2008 | Morita | C02F 1/20 |
| | | | 422/255 |
| 2010/0236320 A1* | 9/2010 | Stehle | G01N 1/2226 |
| | | | 73/19.1 |
| 2013/0275052 A1 | 10/2013 | Loder et al. | |
| 2016/0369214 A1* | 12/2016 | Mosher | C12C 11/003 |

FOREIGN PATENT DOCUMENTS

| | | | | |
|---|---|---|---|---|
| EP | 0509316 A1 * | 10/1992 | | |
| EP | 0717282 A2 * | 6/1996 | | |
| EP | 1762837 A2 * | 3/2007 | ............ | G01N 33/14 |
| TW | 201516390 A * | 5/2015 | | |

\* cited by examiner

METHOD AND APPARATUS FOR DETERMINING THE CONTENT OF A FOREIGN GAS IN A PROCESS LIQUID

CROSS-REFERENCE TO RELATED APPLICATION

This application claims the priority, under 35 U.S.C. § 119, of Austria patent application AT A50384/2020, filed May 6, 2020; the prior application is herewith incorporated by reference in its entirety.

BACKGROUND OF THE INVENTION

Field of the Invention

The present invention relates to a method for determining the content of a foreign gas in a process liquid according to the independent method claim and to an apparatus for performing the method of the invention according to the preamble of the independent apparatus claim.

The determination of gases in fluids from the measurement of pressure and temperature of the specific gas is known from the prior art. For the determination of the concentration of gases dissolved in liquids, such as in particular carbon dioxide in beverages, a relatively large number of often quite different methods and apparatuses, which are commercially available and in use, are known.

For example, manometric methods for measurement of pressure and temperature are known, in which the temperature and the pressure are measured after the equilibrium between fluid to be tested and headspace situated thereabove has been reached or established. The concentration of the measurement gas carbon dioxide $CO_2$ for example is then determined with the aid of a modified Henry and Dalton's equation (eq. 1) (see "Die manometrische Bestimmung des $CO_2$-Gehalts in Getranken" [Manometric Determination of $CO_2$ Content in Beverages], Brauwelt 50, 1991, page 2402 ff.):

$$c_{CO2} = \xi_{CO2} * (p_{Tot} - p_{Cor}) + c_{Cor} \quad \text{(eq. 1)}$$

with
$c_{CO2}$ in g/L (concentration), and
$\xi_{CO2}$ in g/L/bar (solubility).

In the modified Dalton's equation for gases in containers, an additional shaking-pressure correction $p_{Cor}$ and concentration correction $c_{cor}$ is applied here.

The solubility $\xi$ is a substance-specific variable which falls with rising temperature.

The amount of the absorbed gas in a process liquid is, then, dependent on the specific solubility, the pressure and the temperature.

When applying Henry and Dalton's equation, the measurement gas, in particular carbon dioxide, is present in a state of equilibrium between beverage and overlying gas phase. It is known in addition that foreign gases distort the measurement result in this method. In a state of equilibrium of a gas mixture, each dissolved gas component i can be determined via the respective portion of partial pressure as specified in eq. 2:

$$c_i = \xi_i(T) * p_i \quad \text{(eq. 2).}$$

Therefore, the partial pressures of the foreign gases add up with the actual partial pressure of the carbon dioxide to give the total pressure. In the case of beverages, foreign gases are understood to mean especially all gases except carbon dioxide, for example nitrogen, oxygen and laughing gas, which arise because of the production process, are not eliminated or are intentionally added.

A manometric method for determining pressure and temperature in a beverage is, for example, performed by means of the expansion method. In the expansion method, a representative sample of the measurement liquid is introduced into a measurement chamber or removed directly in the process line into a measurement chamber. In the case of measurements on beverage containers, the entire container frequently serves as the measurement chamber. After the measurement chamber has been closed, the liquid sample to be tested is expanded by an increase in the volume of the measurement chamber, for example by a kind of piston syringe or membrane connected to the measurement chamber in a fluid-tight manner and by brief pressure release when measuring in containers. The pressure which ensues after expansion and the sample temperature are then measured. The carbon dioxide content is calculated therefrom according to Henry's law.

If the sample of the liquid in the sealed measurement chamber is expanded, a liquid phase and a gas phase are formed from the originally pure liquid phase in which all the gases, i.e., the measurement gas and also the foreign gases, were dissolved. If the gases have greatly differing solubilities in the sample liquid, then the ratio of the partial pressures of the individual gases in the gas phase will substantially differ from the ratio of the saturation pressures of the dissolved gases in the sample liquid that was originally—i.e., before expansion—present. In general, the greater the decrease in the partial pressure of a gas dissolved in a liquid in the event of a volume increase, the lower its solubility in the liquid.

In the case of beverages, for example: beer or soft drinks in a process line, simple volume increase is usually sufficient for $CO_2$ content measurement in order to determine the amount of dissolved $CO_2$; the portion of foreign gases such as, for example, air, i.e., oxygen and nitrogen, is usually negligible here. The volume increase is preferably within the range from 3% to 10% of the starting volume in the measurement by the expansion method.

In this method, what is thus primarily ascertained is the saturation pressure of the carbon dioxide in the liquid to be analyzed.

However, other gases dissolved in the sample liquid, such as in particular oxygen and also nitrogen, influence the carbon dioxide content ascertained. The apparatuses that are currently commercially available differ from one another inter alia by the nature of sample removal, the design of the measurement chamber and by various measures for quickened attainment of equilibrium, such as, for example, stirrers, etc.

If the foreign-gas or nitrogen content is not neglected or if nitrogen is even added to the beverage, which improves the so-called mouthfeel for certain beer varieties, this limits the applicability of the simple expansion method. Nitrogen or laughing gas is additionally added especially in Irish brewing products and/or soft drinks such as energy drinks and/or sodas. The resultant beer has less carbon dioxide, the mouthfeel is softer and fuller, and the taste notes are rounded, but also somewhat softened. This additional rounding is performed especially in the case of malty roasty beers. The addition of nitrogen with darker varieties is thus also of increasing interest for beer brewers and filling plants. The nitrogen content of the process beer in the production line rises, and this also means that the influence of the nitrogen on $CO_2$ measurement is no longer negligible. In the case of soft drinks or sodas, there are beverages in which what is added is not pure $CO_2$, but a mixture of $CO_2$ and $N_2O$ or nitrous oxide, also referred to as laughing gas.

In the prior art, Austrian patent AT 409673 (B), corresponding to U.S. Pat. Nos. 7,588,210 and 6,874,351, from the applicant itself discloses a method for measuring at least two different gases contained in the fluid and a method for determining the amounts of gases dissolved in the liquid, preferably in a beverage. In AT 409673 (B), the gases are ascertained from a multiple expansion of the measurement volume and associated pressure measurement. In the method, complete filling of the measurement chamber with the liquid to be tested for its gas content ("sample liquid") is followed by increasing the volume thereof—proceeding from a standard volume—by a specified factor and ascertaining the equilibrium pressure which is subsequently reached in the measurement chamber and calculating—on the basis of the pressure measurement value thus obtained—the gas content of the measurement gas in the liquid to be tested. Thereafter, the volume is further increased in at least two or more expansion steps. After each of the volume-increase steps, the equilibrium pressure which is reached in the measurement chamber in each case is ascertained and the concentration/amounts of the individual components is calculated therefrom via a system of equations.

In the case of multiple dissolved gases, there is thus a need for an appropriate number of volume-increase steps and appropriately more extensive calculation methods. If more than one gas has been dissolved in the process liquid and if the solubilities of individual gases are also to be ascertained, what arise are nonlinear systems of equations of higher order which are typically solved iteratively proceeding from estimated values for the unknown gas solubilities, the accuracy of the estimated values being as close to reality as possible. If the solubilities of carbon dioxide and nitrogen in beverages are compared, they are greatly different, and the resulting partial pressure differs substantially, which makes the ascertainment of the nitrogen content possible with the aid of complex mathematics. The ascertainment of nitrous oxide in a beverage containing carbon dioxide and nitrous oxide is not possible with this method, since the solubility of nitrous oxide and carbon dioxide are virtually identical.

Furthermore, methods for determining the concentration of a gas, in which the gas itself is determined without the influence of foreign gases, are known from the prior art. For example, this is possible by means of an optical ATR measurement. The method is based on the evaluation of absorption or transmission spectra, in which the excitation of characteristic molecular vibrations, these being rotation and/or vibration, in the liquid leads to energy absorption and thus to a change in intensity in the excitatory spectrum. With this method, it is possible to ascertain ingredients of low concentration and lowest concentration, with the respective concentration of the ingredient in solid, liquid or gaseous media being ascertained from the absorption of infrared radiation. Depending on the measurement task, use is made of different wavelength regions of the spectrum for structural elucidation; the measurement region ranges from UV/VIS right up into the infrared region. From energy determined from the absorption of radiation, it is possible to deduce the excited molecular or lattice vibrations and thus the constituents of the material tested. Substances sufficiently penetrable for the measurement radiation can be measured in transmission; for opaque solid bodies and for strongly colored solutions, the analysis of reflection such as, for example, with the method of attenuated total reflection (ATR) is known. In process analytics, the applicability of transmission measurements is frequently limited by the strong absorption due to water molecules in the infrared region, and so reflection measurements such as the method of ATR are advantageously used. Spectroscopic determination also shows the advantage that the measurement results are independent of the pressure of the liquid tested and the components thereof. Optical measurement thus shows no cross-sensitivities with respect to substances other than those to be measured.

Austrian patent AT 512291 (B1), corresponding to U.S. patent publication No. 2013/0275052, shows one embodiment for optical measurement of the gas content of fluids, wherein this patent also corrects accurate consideration of portions of extract, which are absorbent and may distort concentration, for an ATR sensor.

Whereas optical measurement devices and simple expansion devices can be integrated without any problems in a process line or in a process with a process liquid, the corresponding devices for multiple expansion and thus the determination of a foreign gas in a process liquid are complex in configuration and can only be operated in so-called bypass. Furthermore, the cleaning of these multiple expansion chambers present in the measurement devices is also very complicated and can lead to hygiene problems especially in the food sector.

The ascertainment of the concentration of nitrogen as foreign gas in carbon dioxide-containing beverages is, in particular, difficult, since there are no suitable measurement devices for this measurement.

The ascertainment of the concentration of nitrous monoxide as foreign gas in carbon dioxide-containing beverages is, in particular, not possible in the double-stroke method, since the gases are not differentiable with said method because of the virtually identical solubility.

BRIEF SUMMARY OF THE INVENTION

It is therefore an object of the invention to provide a method by means of which it is possible to determine a foreign gas in a process liquid in which a measurement gas, especially $CO_2$, has been dissolved. This object is achieved by the method of the invention according to the independent method claim.

According to the invention, what is provided in this connection is the concentration of the measurement gas being ascertained. The concentration of the gas mixture formed by the measurement gas and the foreign gas being ascertained, especially via a manometric measurement method. The measurement values being supplied to an evaluation unit, the concentration of the foreign gas being determined on the basis of the ascertained concentration of the measurement gas and the ascertained concentration of the gas mixture.

According to the invention, what are thus performed are an accurate measurement of the measurement gas and then a measurement of the total pressure and the temperature of the gas mixture formed by the foreign gas and measurement gas. Since the content of the foreign gas is difficult to determine, especially the content of nitrogen, and not determinable, especially the content of nitrous oxide, the method according to the invention determines the content of the process gas, for example the $CO_2$ content, in two different methods, one using an exact method in which the concentration of the measurement gas is exactly determined and using a second method in which the $CO_2$ concentration is deliberately determined with an error owing to the foreign gas. These two methods are then compared with one another and in this way a simple determination of the foreign gas is achieved via comparison of the two measurement values.

In this way, what is provided is a simple measurement method which also allows simple integration within a process line and, at the same time, is cost-effective and has a simple configuration.

Particularly advantageous embodiments of the method according to the invention are defined in greater detail by the features of the dependent claims.

An advantageous measurement or determination of the concentration of the foreign gas is achieved by the total pressure and the temperature of the gas mixture formed by the measurement gas and the foreign gas being ascertained, especially via a manometric measurement method. The partial pressure of the measurement gas is determined on the basis of the ascertained concentration of the measurement gas and the ascertained total pressure and the ascertained temperature. The partial pressure of the foreign gas is ascertained on the basis of the ascertained partial pressure of the measurement gas and on the basis of the measured total pressure and the measured temperature, and the concentration and/or the content of the foreign gas is determined via the partial pressure of the foreign gas.

Advantageously, foreign gas can be added to the process liquid after the ascertainment of the concentration of the measurement gas.

For example, when producing beverages, the foreign gas such as, for example, nitrogen or laughing gas can be added to the beverage liquid or process liquid only in the course of the production process, it being possible for the content or the now present concentration of the foreign gas to be determined in a simple manner via the method according to the invention.

Advantageously, the concentration of the measurement gas can be ascertained by a manometric sensor via a manometric measurement method, especially via an expansion method, preferably with a volume increase of 1% to 20%, particularly preferably with a volume increase of 3% to 10%. The smaller the volume increase, the more rapid the performability of degassing and hence the more rapid the attainment of equilibrium between liquid and gas. The expansion volumes are chosen as follows: the smaller the expansion volumes, the greater the inclusion of volume increase errors in the measurement. Preference is therefore given to using small volume increases in the method according to the invention.

For example, the measurement gas or the gas mixture of measurement gas and foreign gas can be determined via a manometric method before addition of the foreign gas, then the foreign gas can be added to the process liquid and subsequently a manometric measurement method can be performed once again, and the portion of the foreign gas can thus be determined by calculation of the differences between the two measurement values.

In order to be able to achieve an exact, i.e., foreign gas-independent, determination of the concentration of the measurement gas, the concentration of the measurement gas can be ascertained by means of a first sensor designed as an optical sensor, especially as an ATR sensor, wherein especially an optical absorption measurement of the measurement gas is performed by means of the first sensor.

As described in the introduction, the ATR method is already well-known and makes it possible to determine the concentration of, for example, $CO_2$ in the process liquids such as beverages exactly, i.e., without errors, due to the foreign gas, and is therefore advantageously used in the method according to the invention.

Advantageously, the total pressure and the temperature of the gas mixture formed by the measurement gas and the foreign gas can be ascertained by means of a second sensor configured as a manometric sensor and the total pressure can be ascertained via a manometric measurement method, especially via a measurement by the pressure-temperature method or volume expansion method.

As is known from the prior art, a manometric measurement of the total pressure and the temperature of the gas mixture formed by the measurement gas and the foreign gas can be done in a simple manner via a manometric or so-called expansion method. Especially in combination with an optical sensor, for example an ATR sensor, which determines the exact content of the measurement gas, it is possible in this way for the concentration of the foreign gas to be determined in a particularly effective manner and with a simple configuration.

The partial pressure of the foreign gas can be ascertained in a simple manner by the partial pressure of the foreign gas ($P_F$) being ascertained with the aid of the equation $P_F = (p'_{Total} - p_{MG}/(1+v/L_{MG}))*(1+v/L_F)$.

Especially in the case of the measurement of beverages or process liquids in food technology, the measurement gas can be carbon dioxide and the foreign gas can be especially nitrogen or nitrous oxide. This means that the determination of foreign gas can be affected by means of standard sensors for a measurement gas to be frequently measured.

In order to be able to determine even more accurately the portion of the foreign gas and the measurement gas depending on the process liquid, the solubility and/or the compressibility of the measurement gas and/or the foreign gas in the process liquid can be taken into account in the determination of the concentration of the measurement gas and/or the foreign gas.

The measurement or evaluation of the concentration of the measurement gas and the foreign gas can be further improved in that the difference between the measurement values of the two sensors is calibrated using samples of known concentration of measurement gas and foreign gas and these calibration curves or tables are stored in the evaluation unit.

The concentration of the foreign gas can be determined in a particularly simple manner in the case of known and recurring sample liquids, by the relationship between the concentration of the measurement gas without foreign gas influence and the concentration of the gas mixture consisting of measurement gas and foreign gas being determined before the start of measurement on the basis of measurements on known samples, by the values for the foreign-gas concentration being made available in the evaluation unit of the measurement devices as calculation curves and/or table values as the concentration difference of the measurement gas, which concentration difference is especially temperature-dependent, and by the foreign-gas concentration being ascertained on the basis of these values during the measurement.

A preferred application of the method according to the invention in food technology can be achieved by the determination of the concentration of the measurement gas and the measurement of the total pressure and temperature of the gas mixture taking place in a pipe system of the process liquid or in a vessel, especially at a short distance from one another, preferably opposite one another. This can ensure that the measurement conditions of the two sensors are identical and that especially no concentration differences prevail.

The method according to the invention is particularly advantageously applied in the production or monitoring of beverages, wherein the determination of nitrogen or laughing gas in the beverage, such as, for example, beer, can be achieved particularly effectively using the method according to the invention.

Especially in the case of beverages, the process liquid is consistently mixed with extracts or contains extracts or suspended particles which can distort the measurement values. Therefore, according to the invention, the content of extracts contained in the process liquid can be taken into account in the determination of the content of the measurement gas.

The method according to the invention is further improved by the vapor pressure of the process liquid being taken into account in the determination of the concentration of the measurement gas and the foreign gas. As a result of the vapor pressure of the process liquid being taken into account, the accuracy of the determination of the concentrations of foreign gas and measurement gas is improved.

An alternative application of the method can be provided by the process liquid, the measurement gas and the foreign gas being present in a vessel in a two-phase state. The process liquid containing dissolved portions of the measurement gas and the foreign gas form the first phase and an undissolved portion of the measurement gas and the foreign gas form the second phase as a gas mixture. The first sensor and the second are arranged in the region of the vessel in which the measurement gas and the foreign gas are present dissolved in the process liquid.

A further aspect of the invention envisages providing an apparatus, by means of which the method according to the invention can be performed. This object is achieved by the characterizing features of the independent apparatus claim. According to the invention, the apparatus includes a first sensor, by which the content of the measurement gas is ascertainable, and the apparatus contains a sensor, especially a second one, by means of which the total pressure and the temperature of the measurement gas and the foreign gas in the process liquid are ascertainable, especially via a manometric measurement method, and the apparatus contains an evaluation unit configured to perform the method according to the invention.

A particularly exact determination of the measurement gas can be achieved by the sensor being designed as an optical sensor, especially as an ATR sensor.

Advantageously, the sensor, especially the second sensor, can be configured as a manometric sensor, and can be especially configured such that the measurement by the pressure-temperature method or volume expansion method is performable by means of the sensor.

The method according to the invention can be performed in a particularly simple manner by the first sensor and the second sensor being arranged at a short distance from one another, especially opposite one another, in the pipe system, and being installable in the pipe system especially via flanges, or the first sensor and the second sensor being arranged opposite one another in the vessel.

Other features which are considered as characteristic for the invention are set forth in the appended claims.

Although the invention is illustrated and described herein as embodied in a method for determining the content of a foreign gas in a process liquid, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 4:
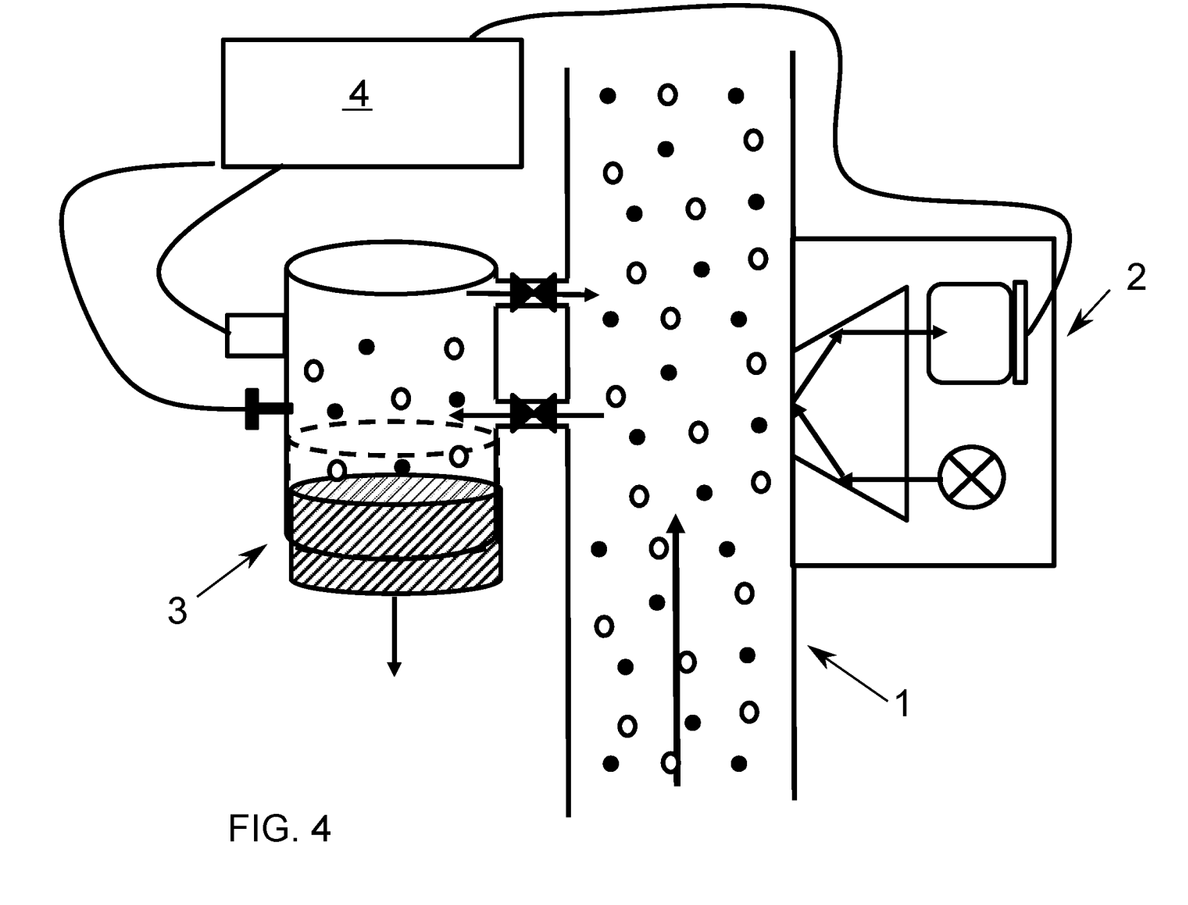
FIG. 4 is an illustration showing a pipe system.

In the following, the apparatus according to the invention and the method according to the invention are described in more detail in FIG. 4. Thus, in a first exemplary embodiment, the apparatus can contain a pipe system 1 which a process liquid flows. Dissolved in the process liquid, for example beer, is a measurement gas, for example carbon dioxide, in this case in low concentration. Integrated in the pipe system 1 is a first sensor 2, by means of which the content of the measurement gas is ascertained as accurately as possible, for example by an optical measurement. Furthermore, the apparatus contains a second sensor 3 for carbon dioxide measurement, configured as a manometric sensor for example, by means of which the total pressure and the temperature of the measurement gas and the foreign gas, i.e., the gas mixture formed from these two gases, in the process liquid is then ascertained. The measurement data of the first sensor 2 and the second sensor 3 are then supplied to an evaluation unit 4, which determines the content of the foreign gas from said measurement data or from the measurement values obtained by the sensors.

For example, according to the invention, the $CO_2$ concentration is determined optically by the first sensor 2 by an ATR method without foreign gas influence and the so-called apparent $CO_2$ content is then ascertained using the second sensor, for example via pressure and temperature measurement, and the apparent $CO_2$ content is then compared with the exactly measured $CO_2$ content. From the twin measurement of $CO_2$ content, the partial pressure and thus the concentration of the foreign gas is then ascertained via the partial pressure or the concentrations of the measured $CO_2$ values by the method according to the invention, for example by means of Henry and Dalton's equation.

The method according to the invention utilizes a measurement value not influenced by the foreign gas for the determination of the exact $CO_2$ concentration, which measurement value is captured using an optical sensor, for example an ATR sensor, and compares the measurement value with the "error-containing" $CO_2$ concentration value from the manometric method in order to infer the partial pressure and the concentration of the foreign gas.

In the following embodiment of the method according to the invention, the first sensor 2, a Carbo 520 from Anton Paar (https://www.anton-paar.com/at-de/produkte/details/carbo-520-optical/), measures the $CO_2$ concentration optically by the ATR method without foreign gas influence. A second sensor 3 for pressure and temperature measurement, Carbo 510 from Anton Paar (https://www.anton-paar.com/corp-de/produkte/details/carbo-510-smart-sensor/), ascertains the apparent or error-containing $CO_2$ content from the measured total pressure. If no second gas is present, the apparent $CO_2$ content corresponds to the actual $CO_2$ content and it is possible, for example, to check whether a foreign gas is contained in the process liquid in the first place.

If the $CO_2$ contents ascertained by the first sensor 2 and the second sensor 3 differ, the partial pressure and the concentration of the foreign gas, for example nitrogen or nitrous oxide, can then be ascertained from the concentration and/or the determined partial pressure of the $CO_2$ on the basis of the following calculation.

In the case of the presence of a foreign gas, the total pressure measured using the manometric method is yielded by the sum totals of the partial pressures.

Dalton's law: $p_{Total} = \Sigma p_i$

The following therefore applies to the $CO_2$ and foreign gas: $p_{Total} = p_{CO2} + p_{FG}$.

The concentration can then be determined using Henry and Dalton's law: $ci = \xi i(T) * pi$
where:
ci is in g/L (concentration of a gas), and
$\xi i$ is in g/L/bar (solubility of a gas).

The $CO_2$ and $N_2O$ concentration can also be specified in the unit "volume" (vol) instead of "g/L". 1 vol=1 liter of $CO_2$ or $N_2O$ under standard pressure (1 bar) per liter of beverage. (The units can be converted via the gas law).

The $CO_2$ concentration is then calculated by: $c_{CO2V} = p_{CO2} * L_{CO2}$
where:
$c_{CO2V}$ ... $CO_2$ concentration in unit of volume,
$L_{CO2}$ ... solubility in volume/bar=$\xi/(M/(R*T0*Z0))$=$\xi$/1.951,
T0=273.2 K, Z0=0.993, $M_{CO2}$=44.01 g/mol, and
R ... gas constant=$8.3145*10-2[l*bar/(K*mol)]$.

From the $CO_2$ concentration value determined using the foreign gas-independent optical sensor, it is possible to infer or back-calculate the true partial pressure of the $CO_2$ $p_{CO2}$:
$p_{CO2} = c_{CO2OPT}/\xi_{CO2}$.

From the manometric total-pressure measurement value for $CO_2$ plus foreign gas and the actual partial pressure of the $CO_2$, it is then possible to infer the partial pressure of the foreign gas and thus also the concentration of any foreign gas such as, for example, nitrogen or laughing gas.

Figure 1:
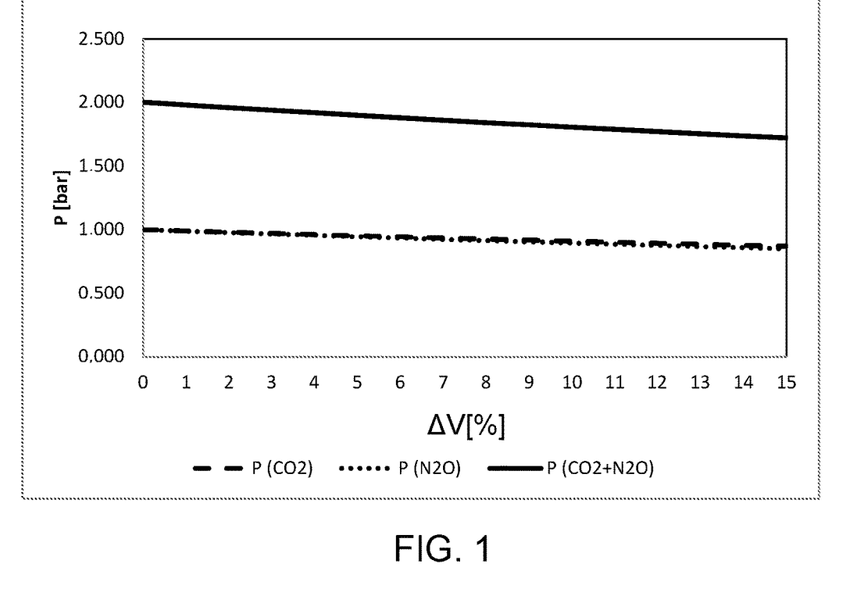
FIG. 1 is a graph showing portions of partial pressures of $CO_2$ and foreign gases nitrogen and laughing gas as a function of a volume increase $\Delta V$ in a measurement by the expansion method.

FIG. 1 shows the differences in the pressure profile of $CO_2$ and the foreign gas nitrogen in the expansion of different volumes. The specific solubility of $N_2$ in beverages such as water or beer is much lower than that of $CO_2$. At a pressure of 1 bar, what can be dissolved in 1 liter of water is 1 liter of $CO_2$ under normal pressure, but only 0.17 liter of nitrogen at the same pressure. This means that the greatest portion of the nitrogen is already in the gas phase in the measurement using the expansion method with, for example, 10% expansion; the influence due to the nitrogen thus rises with small expansion volumes. The nitrogen and $CO_2$ concentration in the liquid falls. The partial pressure of the nitrogen drops rapidly in the expanded chamber compared to the $CO_2$ pressure, meaning that the majority of the foreign gas nitrogen has so to speak diffused out of the solution. The partial pressure then changes only slightly.

The partial pressures reached as a result of a volume increase v can be calculated using a modified Henry and Boyle's formula as described below. In order to simplify the formula, calculations are made with the solubility in "volume/bar" instead of "g/l/bar".

$p'_{CO2} = p_{CO2}/(1+v/L_{CO2})$
$p'_{FG} = p_{FG}/(1+v/L_{FG})$
$p'_x$ partial pressure of the gas after the measurement-chamber volume increase
$p_x$ saturation pressure of the gas in the liquid
Volume increase v=0.1 (=10%)
$L_x$ solubility of the gas in the sample liquid in "volume/bar"

The following apply:
$p'_{Total} = p_{CO2}/(1+v/L_{CO2}) + p_{FG}/(1+v/L_{FG})$
$p_{FG} = (p'_{Total} - p_{CO2}/(1+v/L_{CO2})) * (1+v/L_{FG}))$ For the specific solubility, literature values for the fluids and gases to be tested can be used.

$c_{FG} = \xi_{FG}(T) * p_{FG}$

In the following, a method according to the invention is described exemplarily on the basis of an exemplary embodiment of $CO_2$ as measurement gas and nitrogen as foreign gas.

The first sensor 2 configured as an optical sensor, Carbo 520 from Anton Paar (https://www.anton-paar.com/at-de/produkte/details/carbo-520-optical/), measures the $CO_2$ concentration without foreign gas influence. A second sensor 3 which is configured as the manometric sensor Carbo 510 (https://www.anton-paar.com/corp-de/produkte/details/carbo-510-smart-sensor/) and functions according to the expansion method is used for foreign gas determination, i.e., for nitrogen determination.

The volume increase of the second sensor 3 is set at around 10% in order to minimize measurement errors. A reduction would have the advantage that an error of the optical measurement value has less influence, but that the influence of the volume increase or pressure dependency rises. In this exemplary embodiment, the expansion volume for the manometric sensor is thus advantageously optimally chosen on the basis of the actual specific solubility of the foreign gas to be tested. Alternatively for different gases, the expansion volume can also be adapted thereto and also be chosen differently in the exemplary embodiment described.

From the $CO_2$ concentration ascertained by the first sensor 2 without foreign gas influence, it is possible to calculate the $CO_2$ saturation pressure:

a) $p_{CO2} = c_{(CO2)OPT}/L_{CO2}$

Besides the apparent $CO_2$ value, the second sensor also provides the total pressure according to volume increase: $p'_{Total}$. From both values, it is possible to ascertain the partial pressure of the foreign gas, in this case nitrogen by way of example.

$p_{N2} = (p'_{Total} - p_{CO2}/(1+v/L_{CO2})) * (1+v/L_{N2})$.

For the specific solubility, literature values for the process liquids to be tested can be used.
$ci = \xi i(T) * pi$
The following apply:
Solubilities L at a defined measurement temperature, for example 10° C.:
$L_{CO2}$=1.058 bar−1, $\xi_{CO2}$=2.06 g/L/bar
$L_{N2}$=0.017 bar−1, $\xi_{N2}$=20 mg/L/bar
Saturation pressures in the gas phase: $p_{CO2}$=2. 50 bar, $p_{N2}$=2. 00 bar
For nitrogen as foreign gas, rearrangement and insertion therefore yields:
$p'_{Total} = p_{CO2}/(1+v/L_{CO2}) + p_{N2}/(1+v/L_{FG}) = 2.284 + 0.291 = 2.574$ bar
$p_{N2} = (p'_{Total} - p_{CO2}/(1+v/L_{CO2})) * (1+v/L_{N2}) = 0.290 * 6.882 = 2$ bar
$c_{N2} = \xi_{N2} * p_{N2} = 20*2 = 40$ mg/L An alternative calculation of the content of the foreign gas can also be done with the aid of an empirically ascertained polynomial composed of $CO_2$, apparent $CO_2$ and temperature. The $CO_2$ contents ascertained by the first sensor 2 and the second sensor 3 or the partial pressures calculated therefrom are used for this purpose. The difference between the measured pressure values is studied by measurement of known samples having known contents of $CO_2$ and a defined foreign gas. The different measurement values are measured using standard measurement instruments, for example the CarboQC from the applicant or other highly accurate laboratory devices.

The difference between the thus ascertained CO2 concentrations is ascertained from the difference of $c_{DEV} = c_{(CO2)Man} c_{(CO2)OPT}.$ From this difference, the foreign gas content, for example nitrogen content or laughing gas, is then ascertained and a table containing foreign gas values in relation to respective $c_{DEV}$ at various temperatures is stored in the evaluation unit 4. In the process line, the measured differences are then read from a corresponding lookup table.

The measurement values can optionally also be fitted with a higher order polynomial and be stored in the evaluation unit 3 as calculation curves. The corresponding solubilities, temperatures and pressure differences are evaluated and taken into account:

$c_{N2} = f(c_{DEV}, c_{(CO2)OPT}, t).$

Thus, the relationship between measurement gas concentration without foreign gas influence and measurement gas concentration with foreign gas influence can alternatively be determined in advance at the factory on the basis of measurements on known samples. The values for the foreign-gas concentration are then made available in the evaluation unit of the measurement devices or stored therein as calculation curves and/or table values as the concentration difference of the measurement gas, which concentration difference is especially temperature-dependent. When the concentrations and the pressure and the temperature are measured, the foreign-gas concentration is then ascertained on the basis of these values during the measurement.

The applicable formula is then not universally valid, but only for one process liquid in each case, for example beer, and is, depending on the process liquid to be measured, adapted for, for example, soft drinks and a corresponding formula is developed and stored in the evaluation unit 4. The user can thus select the tested process liquid, for example beer, cola, diet cola, etc., and the foreign gas in the evaluation unit 4 and thus consult the correct evaluation curve.

The evaluation unit can be respectively present in each sensor itself, i.e., the measurement values can be processed directly in an evaluation unit assigned to the sensor or arranged therein or can be supplied to a central evaluation unit in which the measurement values of the sensors are then processed and the determination of the concentration of the foreign gas takes place.

Optionally, accuracy can be improved even in the case of a low $CO_2$ content in the liquid. If the process liquid is expanded in the case of low $CO_2$ concentrations in the process liquid, the pressure which is reached arises not only from the $CO_2$ gas from the process liquid, but also from the water vapor of the aqueous solution, particularly in the case of a large expansion. In order to then increase accuracy, the vapor pressure of the water is also taken into account in the determination of the concentration of the foreign gas; the pressure value ascertained in the measurement of the process gas, for example the measurement of $CO_2$, is therefore corrected:

$p_{Cor} = p_{Gas} - p_{Vapor}.$

This is done using a formula, the Magnus formula, which can be gathered from the literature and takes into account the dependency of the vapor pressure on the measurement temperature.

(Magnus formula for the saturation vapor pressure above level water surfaces:

$p_{Vapor} = 0.006112 * \mathrm{Exp}(17.62 * t/(t+243.12)) (\text{for } -45° \text{ C.} < T < 60° \text{ C.}).$ Furthermore, the accuracy of the method according to the invention can be increased by using the real gas factor or the compressibility factor. The real gas factor or compressibility factor describes the deviation of a real gas from ideal behavior. Gases sometimes considerably deviate from ideal behavior in the case of finite volume and higher pressures.

$m_G = p * V_H * M/(R * T * Z)$ Mass of the gas in the headspace p . . . Partial pressure of $CO_2$
$m_G$ . . . Mass of $CO_2$
$V_H$ . . . Headspace volume
M . . . Molar mass
R . . . Gas constant
T . . . Temperature in K
Z . . . Compressibility
$Z = 1.0005 + p_{Cor} * (-0.007 + T * 0.0000674)$
Z is the compressibility factor of $CO_2$; it is temperature- and pressure-dependent and can in principle be gathered from the literature. When applied, the factor lies in the order of magnitude of 0.98 and plays a greater role, the larger the volume of expansion.

Figure 2:
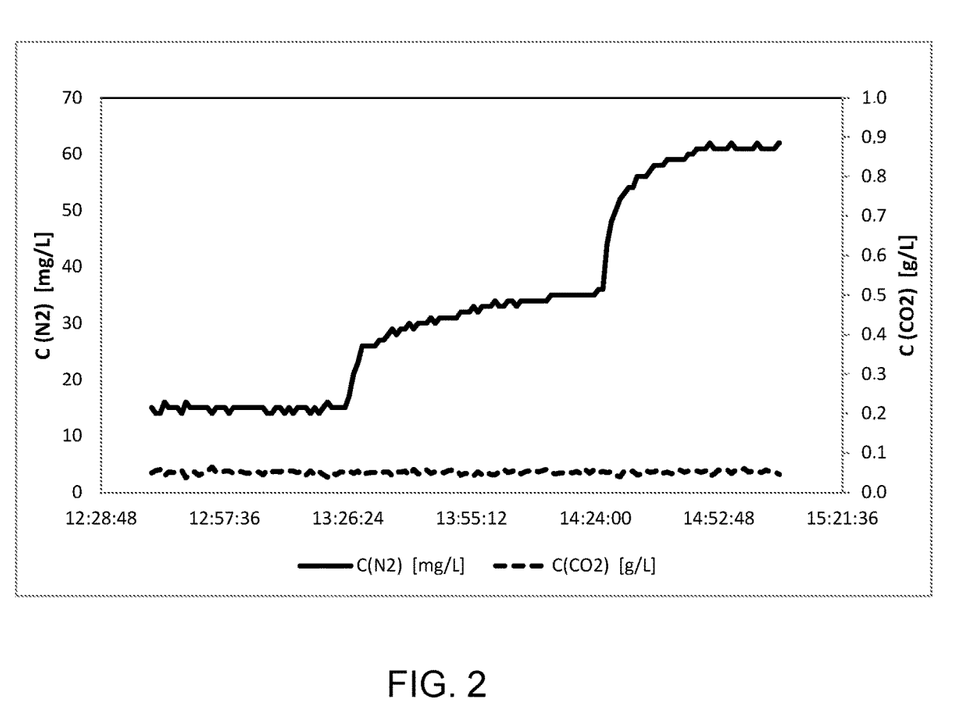
FIGS. 2 and 3 are graphs showing measurement results of an experimental test for determination of a nitrogen content and a laughing-gas content in a process liquid with an aid of the method according to the invention.

FIG. 2 shows the results of an example of nitrogen measurement using the combination of a first optical sensor Carbo520 and a second manometric sensor Carbo510.

The system was started with air-saturated water, which is cooled to 20° C. via a heat exchanger with thermostat.

At two time points, t1 13:25 (1:25 PM) and t2 14:25 (2:25 PM), nitrogen was injected in each case into the fluid tested: the nitrogen concentration determined correlates with the saturation pressure.

Figure 3:
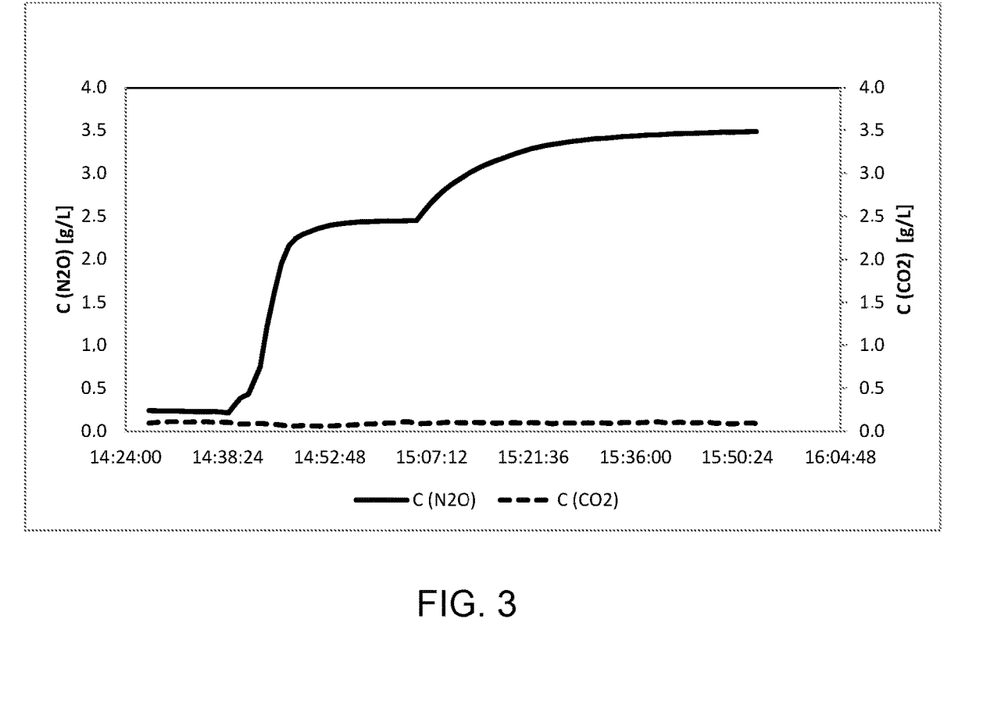

FIG. 3 shows the results of an example of nitrous oxide measurement (laughing gas) using the combination of a first optical sensor Carbo520 and a second manometric sensor Carbo510.

The system was started with water as process liquid, which is cooled to 20° C. via a heat exchanger with thermostat.

At two time points, t1 14:38 (2:38 PM) and t2 15:05 (3:05 PM), nitrous oxide was injected in each case into the process liquid tested. The nitrous oxide concentration determined correlates with the saturation pressure.

As an alternative to the first exemplary embodiment, it is, for example, also possible for the first and/or the second sensor 3 to be arranged within a vessel in which the process liquid is collected. The process liquid, for example beer, is collected in such vessels, for example beverage tanks, and what is formed above the process liquid is a gas phase, the so-called headspace, in which the measurement gas in the undissolved portion is present. Thus, the process liquid, the measurement gas and the foreign gas are present in the vessel in a two-phase state, wherein the process liquid containing dissolved portions of the measurement gas and the foreign gas form the first liquid phase and, thereabove in the headspace, an undissolved portion of the measurement gas and the foreign gas in a gas mixture form the second phase. Here, according to the invention, the first sensor 2 and the second sensor 3 can be arranged in the region of the vessel in which the measurement gas and the foreign gas are present dissolved in the process liquid. The method according to the invention can then be performed according to the invention, as explained in relation to the first exemplary embodiment.

Alternatively, the foreign gas can likewise be added only in the course of the production of the process liquid, for example beer. Thus, alternatively, the content of the measurement gas, for example carbon dioxide, can first be ascertained by means of the first $CO_2$ sensor, for example via the ATR method or an ATR sensor, in order to determine the exact $CO_2$ content within the process liquid. In a further step, the foreign gas, for example nitrogen, is then added and measurement is subsequently performed using the second sensor, for example a manometric sensor, and the content of the foreign gas is then ascertained via the method according to the invention via the measured pressures or determined partial pressures of the measurement gas and the foreign gas.

In a further alternative embodiment of the apparatus according to the invention and the method according to the invention, only one sensor is provided inside the process line or the vessel, and the measurement gas is first determined before addition of a foreign gas and then the process liquid admixed with the foreign gas is guided past the sensor again and a second measurement is performed using said sensor, and, in this way, the added portion of the foreign gas is determined on the basis of the different measurement values.

In the case of the embodiment of the apparatus with two sensors and the performance of the method according to the invention with two sensors, it is particularly preferred that said two sensors, or the measurement points of exact determination of $CO_2$ and of determination of total pressure and temperature, are effected at a short distance from one another or the two sensors are arranged opposite one another in the pipe system 1.

The invention claimed is:

1. A method for determining a content of a foreign gas in a process liquid in which $CO_2$ as a measurement gas has been dissolved, which comprises the steps of:
    using an optical sensor to ascertain a concentration of the $CO_2$ measurement gas either:
        prior to adding the foreign gas to the process liquid, or
        in a gas mixture formed by the measurement gas and the foreign gas;
    using a manometric sensor to obtain an apparent $CO_2$ measurement gas concentration by ascertaining a concentration of the gas mixture formed by the measurement gas and the foreign gas using a manometric measurement method;
    supplying measurement values to an evaluation unit; and
    determining a concentration of the foreign gas on a basis of the concentration of the $CO_2$ measurement gas ascertained by the optical sensor and the apparent $CO_2$ measurement gas concentration ascertained using the manometric sensor.

2. The method according to claim 1, wherein the step of determining the concentration of the foreign gas further comprises the steps of:
    ascertaining a total pressure and a temperature of the gas mixture formed by the measurement gas and the foreign gas;
    determining a partial pressure of the measurement gas on a basis of the concentration of the measurement gas, the total pressure and the temperature;
    ascertaining a partial pressure of the foreign gas on a basis of the partial pressure of the measurement gas and on a basis of the pressure and the temperature; and
    determining a concentration and/or a content of the foreign gas based on the partial pressure of the foreign gas.

3. The method according to claim 2, wherein an optical absorption measurement of the measurement gas is performed by the optical sensor.

4. The method according to claim 3, which further comprises ascertaining the total pressure and the temperature of the gas mixture formed by the measurement gas and the foreign gas using the manometric sensor and the total pressure is ascertained via a manometric measurement method.

5. The method according to claim 4, which further comprises ascertaining the partial pressure of the foreign gas ($P_F$) with an aid of equation $P_F = (p'_{Total} - P_{MG}/(1+v/L_{MG}))*(1+v/L_F)$, wherein:
    $P_{Total}$ total pressure ($CO_2$ plus Foreign Gas)
    $P_{MG}$ (partial) pressure p of the measurement gas
    $P_F$ (partial) pressure of the foreign gas
    V Volume of the head space/measurement chamber
    $L_{MG}$ Solubility L of the measurement gas
    $L_F$ Solubility L of the foreign gas.

6. The method according to claim 2, wherein a determination of the concentration of the measurement gas and the measurement of the total pressure and the temperature of the gas mixture take place in a pipe system of the process liquid or in a vessel.

7. The method according to claim 4, wherein a difference between measurement values of the optical sensor and the manometric sensor is calibrated using samples of known concentration of the measurement gas and the foreign gas and calibration curves or tables are stored in the evaluation unit.

8. The method according to claim 4, wherein the process liquid, the measurement gas and the foreign gas are present in a vessel in a two-phase state, wherein the process liquid containing dissolved portions of the measurement gas and the foreign gas forms a first phase and an undissolved portion of the measurement gas and the foreign gas forms a second phase as the gas mixture, wherein the first sensor and the second sensor are disposed in a region of the vessel in which the measurement gas and the foreign gas are presently dissolved in the process liquid.

9. The method according to claim 1, wherein the foreign gas is added to the process liquid after an ascertainment of the concentration of the measurement gas.

10. The method according to claim 1, wherein the foreign gas is nitrogen or nitrous oxide.

11. The method according to claim 1, which further comprises taking into account a solubility and/or a compressibility of the measurement gas and/or the foreign gas in the process liquid in a determination of the concentration of the measurement gas and/or the foreign gas.

12. The method according to claim 1, which further comprises:
    determining a relationship between the ascertained concentration of the $CO_2$ measurement gas and the ascertained apparent $CO_2$ measurement gas concentration on a basis of measurements made on known samples;
    making available values for the concentration of the foreign gas in the evaluation unit of measurement devices as calculation curves and/or table values as a concentration difference of the measurement gas, the concentration difference being temperature-dependent; and
    ascertaining the concentration of the foreign gas on a basis of the values for the concentration of the foreign gas made available in the evaluation unit by the measurement devices during measurement.

13. The method according to claim 1, wherein the process liquid is a beverage containing dissolved gases.

14. The method according to claim 1, wherein a content of ingredients that are contained in the process liquid is taken into account in a determination of the content of the measurement gas.

15. The method according to claim 1, which further comprises taking into account a vapor pressure of the process liquid in a determination of the concentration of the measurement gas and the foreign gas.

16. An apparatus for determining a content of a foreign gas in a process liquid in which $CO_2$ as a measurement gas has been dissolved, the apparatus comprising:
- a pipe system in which the process liquid can flow and/or a vessel in which the process liquid is collectable;
- an optical sensor by which a content of the $CO_2$ measurement gas is ascertained;
- a manometric sensor by which a total pressure and a temperature of the $CO_2$ measurement gas and the foreign gas in the process liquid are ascertained using a manometric measurement method;
- an evaluation unit configured to determine the content of the foreign gas in the process liquid in which the $CO_2$ measurement gas has been dissolved, said evaluation unit configured to:
  - ascertain a concentration of the $CO_2$ measurement gas using information from said optical sensor;
  - ascertain an apparent $CO_2$ measurement gas concentration of a gas mixture formed by the measurement gas and the foreign gas using information from said manometric sensor;
  - receive measurement values; and
  - determine a concentration of the foreign gas on a basis of the concentration of the $CO_2$ measurement gas ascertained and the apparent $CO_2$ measurement gas concentration ascertained.

17. The apparatus according to claim 16, wherein said optical sensor and said manometric sensor are disposed apart from one another in said pipe system.

18. The apparatus according to claim 16, wherein said optical sensor and said manometric sensor are disposed opposite one another in said vessel.

* * * * *